United States Patent [19]

Hayakawa et al.

[11] Patent Number: 5,122,487

[45] Date of Patent: Jun. 16, 1992

[54] SOLID ELECTROLYTE OF PARTIALLY STABILIZED ZIRCONIA AND METHOD OF PRODUCING SAME

[75] Inventors: Nobuhiro Hayakawa; Hiroyuki Ishiguro; Takeshi Kitano; Yutaka Adachi, all of Aichi, Japan

[73] Assignee: NGK Spark Plug Co., Ltd., Nagoya, Japan

[21] Appl. No.: 649,329

[22] Filed: Feb. 4, 1991

Related U.S. Application Data

[63] Continuation of Ser. No. 337,837, Apr. 14, 1989, abandoned.

[30] Foreign Application Priority Data

Apr. 27, 1988 [JP] Japan .................. 63-105160

[51] Int. Cl.⁵ .............................................. C04B 35/48
[52] U.S. Cl. ........................................ 501/103; 501/152; 423/608
[58] Field of Search ............... 501/103, 104; 429/30, 429/46, 189, 190, 193; 204/424; 423/608

[56] References Cited

U.S. PATENT DOCUMENTS

| | | | |
|---|---|---|---|
| 3,334,962 | 8/1967 | Clearfield | 423/608 |
| 4,360,598 | 11/1982 | Otagiri et al. | 501/103 |
| 4,370,393 | 1/1983 | Watanabe et al. | 429/193 |
| 4,664,894 | 5/1987 | Suzuki et al. | 423/608 |

FOREIGN PATENT DOCUMENTS

3537709A1  4/1986  Fed. Rep. of Germany.

OTHER PUBLICATIONS

Ralph Petrucci, *General Chemistry: Principles and Modern Applications* (1982), 403–404.

*Primary Examiner*—William R. Dixon, Jr.
*Assistant Examiner*—Melissa Bonner
*Attorney, Agent, or Firm*—Foley & Lardner

[57] ABSTRACT

As a solid electrolyte suitable for use in oxygen sensors a partially stabilized zirconia, which essentially consists of 4.5–6.0 mol % of $Y_2O_3$ and the balance of $ZrO_2$ and is constituted of tetragonal and cubic crystals, is produced by using a coprecipitated powder of a solid solution of $ZrO_2$ and $Y_2O_3$ as the raw material and performing sintering of a green body at a temperature not higher than 1500° C. The $ZrO_2$-$Y_2O_3$ powder has a mean particle size not larger than 1 μm and a specific surface area in the range from 2.5 to 7 m²/g and is required to be not more than 0.2 wt % in the content of unwanted $SiO_2$ so that the sintered solid electrolyte may be as low as possible in the content of $SiO_2$. The obtained solid electrolyte has good mechanical properties and exhibits sufficiently high withstand voltage.

5 Claims, 2 Drawing Sheets

SOLID ELECTROLYTE OF PARTIALLY STABILIZED ZIRCONIA AND METHOD OF PRODUCING SAME

This application is a continuation of application Ser. No. 07/337,837, filed Apr. 14, 1989 abandoned.

BACKGROUND OF THE INVENTION

This invention relates to an oxygen ion conductive solid electrolyte, which is a partially stabilized zirconia essentially consisting of $ZrO_2$ and $Y_2O_3$ that is suitable for use in oxygen sensors or oxygen sensitive elements of air/fuel ratio detectors to be disposed in exhaust systems of combustion engines, and a method of producing same.

In using $ZrO_2$ as an oxygen ion conductive solid electrolyte it is usual to stabilize or partially stabilize zirconia with addition of a suitable oxide which forms a solid solution with zirconia, and $Y_2O_3$ has widely been used as the stabilizing oxide. Stabilized zirconia, which consists of cubic crystals, is relatively low in thermal shock resistance and hence is liable to crack when subjected to rapid heating. For improvement in this regard, partially stabilized zirconia consisting of cubic, tetragonal and monoclinic crystals has been developed.

However, in a specific region of temperature (200°-300° C.) partially stabilized zirconia undergoes aging deterioration and consequently lowers in mechanical strength. The fundamental cause of this problem is the transformation of tetragonal crystal grains in partially stabilized zirconia into monoclinic crystal grains. The transformation is accompanied by some expansion of the volume of the ceramic body, and the volumetric expansion causes micro-cracks.

To solve the problem of aging deterioration of partially stabilized zirconia, JP-A 56-134564 proposes producing a partially stabilized zirconia which contains $Y_2O_3$ that is mainly constituted of tetragonal crystals and cubic crystals (but may include some monoclinic crystals) by taking measures to make the crystal grains of the sintered product smaller than 2 μm in mean grain size to thereby prevent transformation of the tetragonal crystals to monoclinic crystals. It is intended to reduce the crystal grain size in the sintered product by accomplishing sintering at a relatively low temperature, considering that sintering at temperatures above 1500° C. causes unwanted growth of crystal grains and hence gives a sintered body which contains relatively large crystal grains and is relatively low in mechanical strength and thermal shock resistance. According to the need a sintering aid such as silica or alumina is used.

JP 60-5548 shows using silica and alumina jointly as sintering aids in producing a solid electrolyte of zirconia partially stabilized by yttria.

However, we have recognized that solid electrolytes of partially stabilized zirconia hitherto developed are too low in withstand voltage. When the partially stabilized zirconia is used as a solid electrolyte of, for example, an oxygen ion pump element of an oxygen sensor a so-called blackening phenomenon occurs even at a voltage lower than 3 V whereby the oxygen sensor can no longer perform accurate detection of oxygen concentrations. In our view the primary reason for the insufficiency of withstand voltage is the presence of a considerable amount of $SiO_2$ in the $ZrO_2$-$Y_2O_3$ solid electrolyte.

SUMMARY OF THE INVENTION

It is an object of the present invention to provide an oxygen ion conductive solid electrolyte of a partially stabilized zirconia using yttria as the stabilizing oxide, which solid electrolyte can be obtained by sintering at a relatively low temperature and exhibits good mechanical properties and a high withstand voltage in regard to the blackening phenomenon.

It is another object of the invention to provide a method of producing a solid electrolyte of a partially stabilized zirconia having the above merits.

According to the invention there is provided an oxygen ion conductive solid electrolyte, which is a sintered solid solution of $ZrO_2$ and $Y_2O_3$ and essentially consists of tetragonal crystal grains and cubic crystal grains, wherein the molar ratio of $Y_2O_3$ to $ZrO_2$ is in the range from 4.5:5.5 to 6.0:94.0 and wherein the content of $SiO_2$ as an inevitable impurity is not more than 0.2 wt %.

Furthermore, the invention provides a method of producing a solid electrolyte according to the invention, the method comprising the steps of forming a powder of a solid solution of 4.5 to 6.0 mol % of $Y_2O_3$ and the balance of $ZrO_2$ prepared by a coprecipitation process into a green body of a desired shape, and sintering the green body at a temperature not higher than 1500° C. In this method the $ZrO_2$-$Y_2O_3$ powder has a mean particle size not larger than 1.0 μm and a specific surface area in the range from 2.5 to 7 m²/g and is not more than 0.2 wt % in the content of unwanted $SiO_2$.

In the present invention the $Y_2O_3$/$ZrO_2$ molar ratio is limited within the aforementioned range in order to obtain a partially stabilized zirconia which is a mixed phase of stable tetragonal crystal grains and cubic crystal grains and has good mechanical and electrical properties. A coprecipitated $ZrO_2$-$Y_2O_3$ powder is used as the raw material in view of its good sinterability, and the particle size of this powder is specified as stated above in respect of mean particle size and specific surface area for the purpose of accomplishing sintering at a temperature not higher than 1500° C. without using $SiO_2$ or any other alternative sintering aid and for obtaining a sintered product constituted of fine crystal grains of tetragonal zirconia and cubic zirconia.

In this invention it is desired that the partially stabilized zirconia be free of $SiO_2$. In practice, however, it is inevitable that a very small amount of $SiO_2$, which may be contained in the raw materials or may originate from the balls or linings of mixing apparatus, remain in the sintered product. In view of this fact the content of $SiO_2$ is limited to 0.2 wt % at the maximum.

A solid electrolyte of partially stabilized zirconia according to the invention is fairly small in crystal grain size since sintering is accomplished at a relatively low temperature. Accordingly this solid electrolyte is sufficiently high in mechanical strength. Furthermore, this solid electrolyte is high in thermal shock resistance and hardly undergoes aging deterioration even in the aforementioned temperature range of 200°-300° C. as a result of partially stabilized zirconia consisting of cubic crystals and tetragonal crystals. Further, by virtue of substantially excluding $SiO_2$ this solid electrolyte does not suffer from an increase in electrical resistivity resulting from formation of a silica base vitreous grain boundary phase. In other words, this solid electrolyte is enhanced in electrical conductivity. When this solid electrolyte is used in an oxygen pump element or the like the element is fairly high in withstand voltage, and the solid electrolyte is fairly low in susceptibility to deterioration by blackening.

DETAILED DESCRIPTION OF THE INVENTION

In this invention the molar ratio of $Y_2O_3$ to $ZrO_2$ is limited within the range from 4.5:95.5 to 6.0:94.0 for the purposes explained hereinbefore. If the amount of $Y_2O_3$ is less than 4.5 mol % the partially stabilized zirconia contains more than 60 wt % of tetragonal crystal grains and therefore becomes low in electrical conductivity and undergoes considerable deterioration by aging. If the amount of $Y_2O_3$ exceeds 6 mol % the proportion of tetragonal crystal grains in the partially stabilized zirconia becomes less than 10 wt %, and hence the solid electrolyte is insufficient in mechanical strength and thermal shock resistance.

The $ZrO_2$-$Y_2O_3$ solid solution powder prepared by a coprecipitation process is required to be not larger than 1.0 μm in mean particle size, because if the mean particle size is larger the powder cannot be well sintered at a temperature lower than 1500° C. without using any sintering aid. It is essential to use a powder not larger than 1.0 μm in mean particle size to produce a sintered body of $ZrO_2$-$Y_2O_3$ constituted of a mixture of fine cubic crystal grains and fine tetragonal crystal grains without relying on $SiO_2$ or any other sintering aid.

Furthermore, it is necessary to limit the specific surface area of the $ZrO_2$-$Y_2O_3$ powder within an appropriate and relatively narrow range for achieving complete sintering at a temperature not higher than 1500° C. without using any sintering aid.

Figure 1:
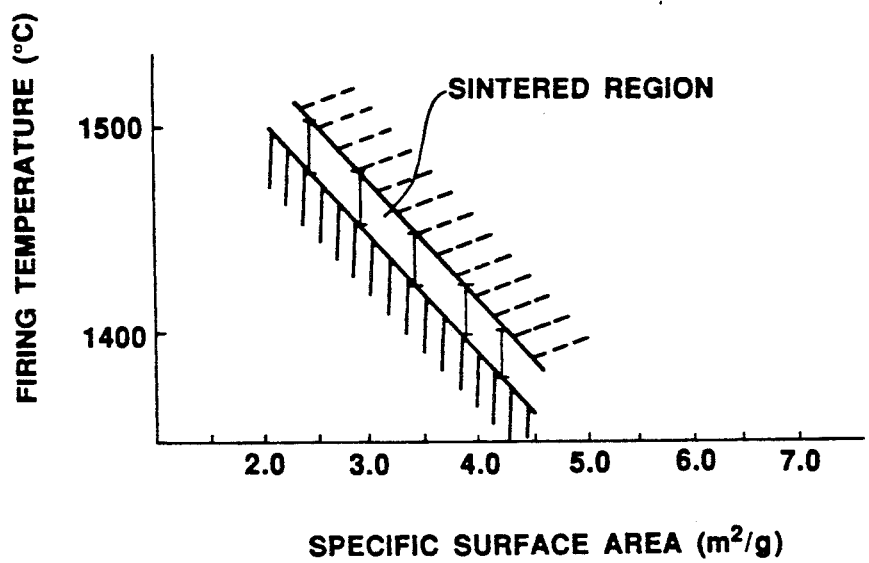
FIG. 1 is a graph showing the dependence of the sinterability of a coprecipitated $ZrO_2$-$Y_2O_3$ powder on its specific surface area and the firing temperature.

FIG. 1 shows the result of an experiment on the sinterability of coprecipitated $ZrO_2$-$Y_2O_3$ powders similar in chemical composition and different in specific surface area. In every powder the molar ratio of $Y_2O_3$ to $ZrO_2$ was 5.5:94.5, and the content of $SiO_2$ was controlled to 0.03 wt %. Every powder was compacted into green bodies and fired at various temperatures not higher than 1500° C. A judgment was made that good sintering was accomplished when the fired body had an apparent specific gravity of 5.8 or above. The experimental result in FIG. 1 indicates that a $ZrO_2$-$Y_2O_3$ powder not smaller than 2.5 m²/g in specific surface area should be used if it is intended to accomplish good sintering at a temperature not higher than 1500° C. On the other hand, it was evidenced that when specific surface area of $ZrO_2$-$Y_2O_3$ powder is larger than 7 m²/g the amount of shrinkage of the fired body is too large to keep desired accuracy of the shape and dimensions of the sintered body.

Figure 2:
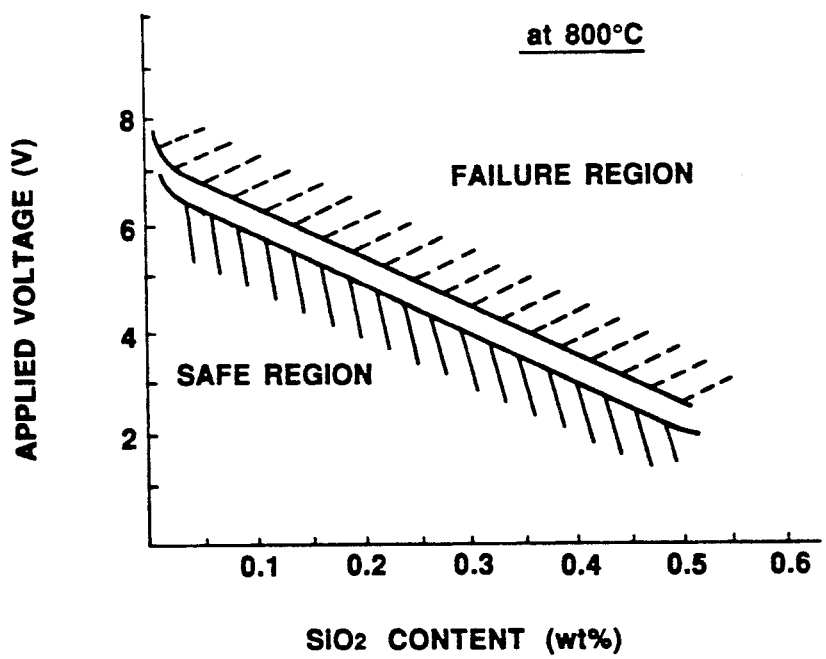
FIGS. 2 and 3 are graphs showing the dependence of withstand voltage of a $ZrO_2$-$Y_2O_3$ solid electrolyte on the content of $SiO_2$.
Figure 3:
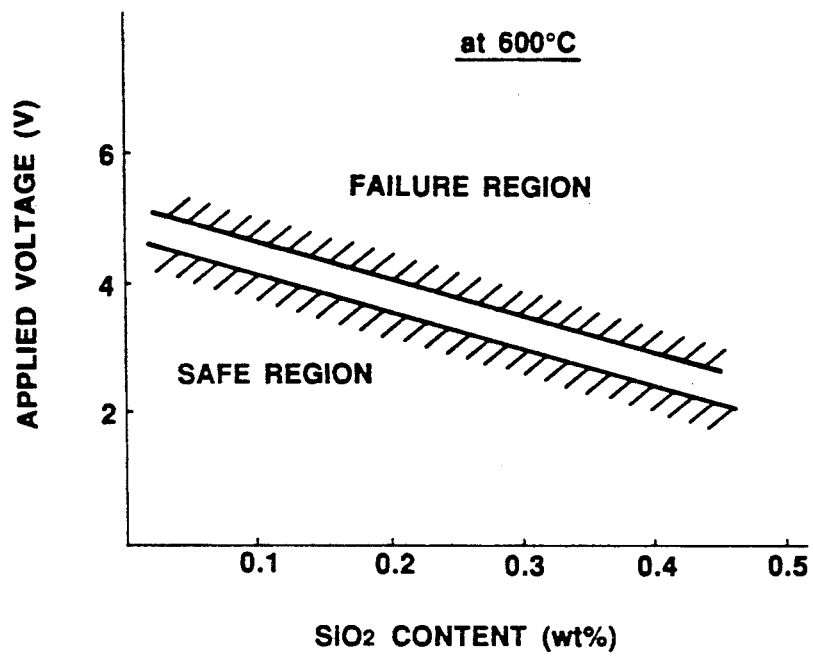

According to the invention the content of $SiO_2$ in the solid electrolyte (and also in the powder employed as the sintering material) is strictly limited to 0.2 wt % at the maximum, because we have proved that $ZrO_2$-$Y_2O_3$ solid electrolyte becomes more susceptible to blackening by application of a low voltage as the content of $SiO_2$ increases. FIGS. 2 and 3 show the results of an experiment on this matter. Samples of $ZrO_2$(94.5 mol %)-$Y_2O_3$(5.5 mol %) solid electrolytes in the form of a thin plate with an electrode layer on each side thereof were produced by adding various amounts of $SiO_2$ to the raw material powder. The samples were divided into two groups to test the samples of one group at 800° C. and the other at 600° C., in the air in the both cases. The withstand voltage of each sample was determined by gradually augmenting a DC voltage applied between the two electrods on the sample until occurrence of the blackening phenomenon. As can be seen in FIGS. 2 and 3, the level of a critical voltage or withstand voltage above which the solid electrolyte undergoes blackening ("failure region" in FIGS. 2 and 3) shifts downward as the content of $SiO_2$ increases.

Solid electrolyte oxygen sensors are largely used in automobiles, and a prevailing power source voltage on automobiles is 5 V. When an oxygen sensor having an oxygen ion pump element of a zirconia solid electrolyte is used as an air/fuel ratio detector which can detect both super-stoichiometric and sub-stoichiometric air/fuel ratios, the polarity of a DC voltage applied to the pump element is chosen according to the range of air/fuel ratios to be detected. That is, it should be expected that, at the maximum, voltages of ±5 V are applied to the solid electrolyte in the oxygen sensor. Therefore, the withstand voltage of the solid electrolyte needs to be at least ±2.5 V and, taking into consideration inevitable deterioration by long use under high temperature conditions, should reach 3-4 V at 600° C. For this reason and in view of the results of extensive experiments, a solid electrolyte according to the invention is required to be not more than 0.2 wt %, and preferably not more than 0.1 wt %, in the content of $SiO_2$.

In this invention it is suitable to perform sintering of the $ZrO_2$-$Y_2O_3$ powder formed into a green body at a temperature ranging from 1400° to 1500° C.

EXAMPLE 1

A mixed oxide powder consisting of 5.5 mol % of $Y_2O_3$ and the balance of $ZrO_2$ was prepared by a usual coprecipatation process. The precipitation conditions were controlled such that the obtained oxide powder was 0.5 μm in mean particle size and 3.3 m²/g in specific surface area.

As a binder, a small amount of polyvinyl butyral in the form of a solution in an organic solvent was added to and mixed with the $ZrO_2$—$Y_2O_3$ powder. The mixing operation was performed so as to minimize intrusion of $SiO_2$ and $Al_2O_3$ into the mixture from the mixing apparatus. After the mixing operation, analysis of the powder (dried sample) revealed that the content of $SiO_2$ was less than 0.1 wt %, and the content of $Al_2O_3$ was less than 0.5 wt %. The wet mixture was shaped by a doctor blade method into a strip of a green sheet about 0.4 mm in thickness, 56 mm in length and 5 mm in width. After drying the green sheet strip, a conductive paste comprised of a Pt powder, a $ZrO_2$-$Y_2O_3$ powder and a binder solution was applied by screen printing to a predetermined region of each major surface of the green sheet strip. The conductive paste was applied for the purpose of providing electrode layers to the sintered product. After that the green sheet strip was subjected to moderate heating for decomposing and removing the binders, and then the green sheet strip was fired in air at about 1450° C. to accomplish sintering. The product of this process was an oxygen ion pump element consisting of a partially stabilized zirconia plate to serve as an oxygen ion conductive solid electrolyte layer and a pair of electrode layers formed on the two opposite sides of the solid electrolyte plate.

COMPARATIVE EXAMPLE

To produce an oxygen ion pump element, the process of Example 1 was repeated except that the raw material and the process conditions were changed in the following points. In this case the $ZrO_2$-$Y_2O_3$ powder had a mean particle size of 1.3 μm and a specific surface area of 3.2 m$^2$/g. After mixing with the binder the powder (dried sample) contained 0.4 wt % of $SiO_2$ and 3.0 wt % of $Al_2O_3$.

EVALUATION TESTS

The oxygen ion pump elements produced in Example 1 and Comparative Example were tested by the following methods.

As a first test, in a high temperature atmosphere of 800° C. a DC voltage of 1.5 V was applied between the two opposite electrodes of each element to measure the current density in the solid electrolyte layer. In the samples of Example 1 the current density ranged from 70 to 75 mA/15 mm$^2$ (surface area of the electrodes), whereas in the samples of Comparative Example the current density was 18 to 30 mA/15 mm$^2$. That is, the performance of the solid electrolyte of Example 1 was 2.5 to 3 times higher than that of Comparative Example. Probably the remarkable rise in the current density in Example 1 was attributed to a considerable rise in the electric conductivity of the sintered solid electrolyte as the effect of reduced contents of $SiO_2$ and $Al_2O_3$.

As another test, the withstand voltage of each oxygen ion pump element was measured in a high temperature atmosphere of 800° C. by gradually augmenting a DC voltage applied between the two opposite electrodes until occurrence of a blackening phenomenon. The samples of the solid electrolyte element of Example 1 exhibited withstand voltages of 7.8 to 8.8 V, whereas the samples of Comparative Example could withstand only to the extent of 2.5 to 3.5 V. It is believed that the remarkably higher withstand voltages of the samples of Example 1 were attributed primarily to the reduced content of $SiO_2$.

EXAMPLE 2

Sintered plates of partially stabilized zirconia were produced by fundamentally the same process as in Example 1, except that the molar ratio of $Y_2O_3$ to $ZrO_2$ were varied to obtain three kinds of solid electrolyte plates in which the $Y_2O_3$/$ZrO_2$ molar ratio was 4.5/95.5, 5.5/94.5 and 6.0/94.0, respectively. For an experimental purpose another solid electrolyte plate was produced by lowering the $Y_2O_3$/$ZrO_2$ molar ratio to 4.0/96.0.

Figure 4:
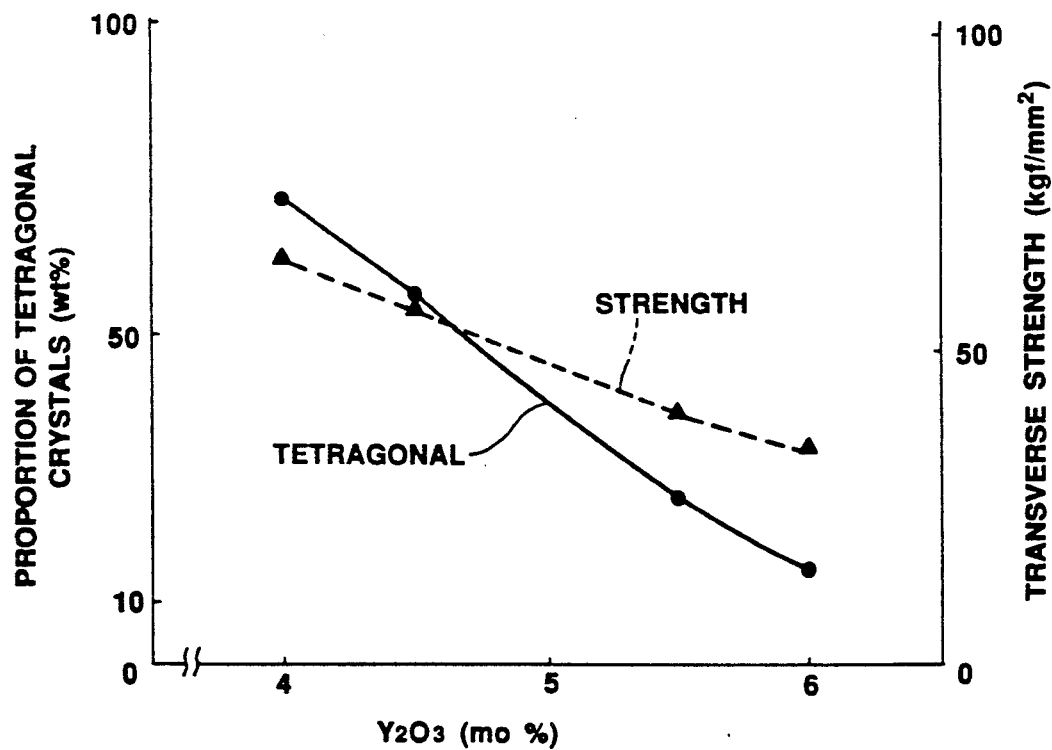
FIG. 4 is a graph showing the dependence of the proportion of tetragonal crystals in a $ZrO_2$-$Y_2O_3$ solid electrolyte and transverse strength of the solid electrolyte on the content of $SiO_2$.

Test pieces of these solid electrolyte plates were subjected to measurement of transverse strength by the standard three-point flexural method. The results are shown in FIG. 4.

Besides, each solid electrolyte was subjected to X-ray diffraction analysis to determine the proportion of tetragonal crystal grains from a ratio between integrated intensities of reflections. That is, the following equation was employed to determine the proportion, T (wt %), of tetragonal crystal grains to the whole crystal grains.

$$T(\text{wt }\%) = \frac{T(400) + T(004)}{C(400) + T(400) + T(004)} \times 100$$

wherein T(400) is the integrated intensity of reflection from (400) plane of tetragonal crystals, T(004) is the integrated intensity for (004) plane of tetragonal crystals, and C(400) is the integrated intensity for (400) plane of cubic crystals.

The results of the analysis are shown in FIG. 4. The curves in FIG. 4 indicate that when the proportion of tetragonal crystals, T (wt %), in the solid electrolyte (partially stabilied zirconia) is less than 15 wt % the deflective strength of the solid electrolyte plate is lower than that of an alumina plate. In practical gas sensor elements or oxygen pump elements using a zirconia solid electrolyte it is usual to employ an alumina substrate with a heater attached thereto. Therefore, it is undesirable that the solid electrolyte is weaker in mechanical strength than alumina. With consideration of this matter, it is desirable that the proportion of tetragonal crystals, T (wt %), in a partially stabilized zirconia according to the invention is at least 15 wt %.

What is claimed is:

1. A method of producing an oxygen ion conductive solid electrolyte which is a sintered solid solution of $ZrO_2$ and $Y_2O_3$ consisting essentially of 15-60 wt % of tetragonal crystal grains and the balance of cubic crystal grains, wherein the molar ratio of $Y_2O_3$ to $ZrO_2$ is in the range from 4.5:95.5 to 6.0:94.0, the method comprising the steps of:

mixing a powder of a solid solution of 4.5 to 6.0 mol % of $Y_2O_3$ and the balance of $ZrO_2$ prepared by a coprecipitation process with a binder and forming the resulting mixture into a green body of a desired shape, said powder having a mean particle size not larger than 1.0 μm and a specific surface area in the range from 2.5 to 7 m$^2$/g and not more than 0.2 wt % in the content of $SiO_2$ as an inevitable impurity; and sintering said green body at a temperature not higher than 1500° C.

2. A method according to claim 1, wherein said content of $SiO_2$ is not more than 0.1 wt %.

3. A method as claimed in claim 1, wherein the molar ratio of $Y_2O_3$ to $ZrO_2$ is about 5.5:94.5.

4. A method as claimed in claim 1, wherein the mean particle size is not larger than about 0.5 μm.

5. A method as claimed in claim 1, wherein the specific surface is about 3.3 m$^2$/g.